United States Patent
Son (10) Patent No.: US 11,071,448 B2
(45) Date of Patent: Jul. 27, 2021

(54) LENGTH ADJUSTABLE CANNULA

(71) Applicant: Conmed Corporation, Utica, NY (US)

(72) Inventor: Jung-Wan Son, Gunpo-si (KR)

(73) Assignee: Conmed Corporation, Utica, NY (US)

( * ) Notice: Subject to any disclaimer, the term of this patent is extended or adjusted under 35 U.S.C. 154(b) by 107 days.

(21) Appl. No.: 14/466,726

(22) Filed: Aug. 22, 2014

(65) Prior Publication Data
US 2014/0364697 A1 Dec. 11, 2014

Related U.S. Application Data (63) Continuation-in-part of application No. 13/429,698, filed on Mar. 26, 2012, now abandoned.

(51) Int. Cl.
*A61B 1/32* (2006.01)
*A61M 39/02* (2006.01)
*A61B 17/34* (2006.01)

(52) U.S. Cl.
CPC ............ *A61B 1/32* (2013.01); *A61B 17/3421* (2013.01); *A61B 17/3423* (2013.01);
(Continued)

(58) Field of Classification Search
CPC . A61B 17/02; A61B 17/0218; A61B 17/3421; A61B 17/3423; A61B 17/864; A61B 2017/3425–3429; A61B 2017/3431; A61B 2017/3443; A61B 2017/3445; A61B 2017/345; A61B 2017/3454; A61B 2017/3456; A61B 2017/3458; A61B 2017/346; A61B 2017/348; A61B 2017/3482; A61B 2017/3492; A61B 2017/867; A61B 2017/8675; A61B 2017/868; A61B 1/32; A61M 5/46; A61M 5/3271; A61M 5/329; A61M 5/344; A61M 5/345
See application file for complete search history.

(56) References Cited

U.S. PATENT DOCUMENTS

| | | | | |
|---|---|---|---|---|
| 3,402,710 A | * | 9/1968 | Paleschuck | A61M 39/0606 128/887 |
| 5,064,417 A | * | 11/1991 | Andreussi | A61M 39/0247 604/175 |

(Continued)

FOREIGN PATENT DOCUMENTS

KR 101090665 B1 * 12/2011 ........ A61M 39/0247

*Primary Examiner* — Amy R Sipp
(74) *Attorney, Agent, or Firm* — Bond, Schoeneck & King, PLLC; Frederick J. M. Price (57) ABSTRACT

A length adjustable cannula includes: a pipe-like main body having a through hole formed therein and an outer circumferential surface on which a screw thread is formed; a base grip provided at an end of the main body; an inner support plate provided at another end of the main body; and an outer support plate thread-coupled with the outer circumferential surface of the main body, the outer support plate being movable along the screw thread in a lengthwise direction of the main body. A position of the outer support plate is adjusted based on a distance from an outside skin to a medical treatment region of a human body, such that the outer support plate is brought into contact with the outside skin and the inner support plate is brought into contact with and supported by an inside skin of the human body.

4 Claims, 9 Drawing Sheets

(52) U.S. Cl.
CPC ... *A61M 39/0247* (2013.01); *A61B 2017/348* (2013.01); *A61B 2017/349* (2013.01); *A61B 2017/3443* (2013.01); *A61B 2017/3482* (2013.01); *A61B 2017/3492* (2013.01); *A61M 2039/0261* (2013.01); *A61M 2039/0273* (2013.01); *A61M 2039/0279* (2013.01)

(56) References Cited

U.S. PATENT DOCUMENTS

| | | | |
|---|---|---|---|
| 7,153,319 B1 * | 12/2006 | Haberland | A61B 17/3462 606/185 |
| 2005/0049624 A1 * | 3/2005 | Francese | A61B 17/3421 606/185 |
| 2009/0012477 A1 * | 1/2009 | Norton | A61B 17/3421 604/174 |
| 2009/0221968 A1 * | 9/2009 | Morrison | A61B 17/3423 604/164.11 |
| 2010/0256453 A1 * | 10/2010 | Hammond | A61B 17/3462 600/210 |
| 2011/0028796 A1 * | 2/2011 | Blinman | A61B 17/3421 600/227 |
| 2011/0034775 A1 * | 2/2011 | Lozman | A61B 17/1684 600/204 |

* cited by examiner

(a) Cannula without flange

Camera image (b) Cannula with flange

Camera image

LENGTH ADJUSTABLE CANNULA

CROSS REFERENCE

This is a continuation-in-part of application Ser. No. 13/429,698, filed on Mar. 26, 2012, which claims foreign priority of Korean Patent Application No. 10-2011-0046980, filed May 18, 2011. The content of each and every one of the foregoing patent applications is hereby incorporated by reference in its entirety.

BACKGROUND OF THE INVENTION

1. Field of the Invention

The present invention relates to a medical cannula to be inserted into a human body when a medical treatment is performed thereon to thereby connect the inside and the outside of the human body; and, more particularly, to a length adjustable cannula allowing a stable installation irrespective of a distance from an outside skin to a medical treatment region of the human body, by adjusting a position of an outer support plate based on the distance such that the outer support plate is brought into contact with and supported by the outside skin and an inner support plate inserted into the human body is brought into contact with and supported by an inside skin.

2. Background of the Invention

In general, a medical cannula is shaped as a small tube or an insertion pipe, and secures an incision portion when a skin of the human body is incised and the cannula is fixedly-inserted into the human body. Once the cannula is fixedly-inserted into the human body, medical instruments are inserted into a through hole formed in the cannula and a medical treatment is carried out.

Figure 1:
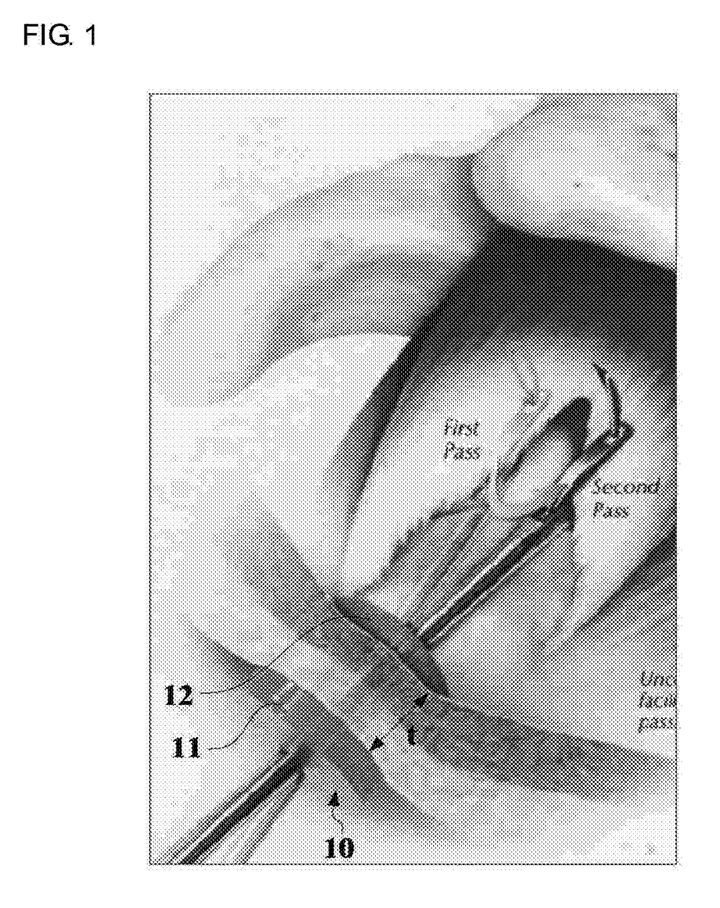
FIG. 1 illustrates a rotator cuff operation using a conventional cannula.
Figure 2:
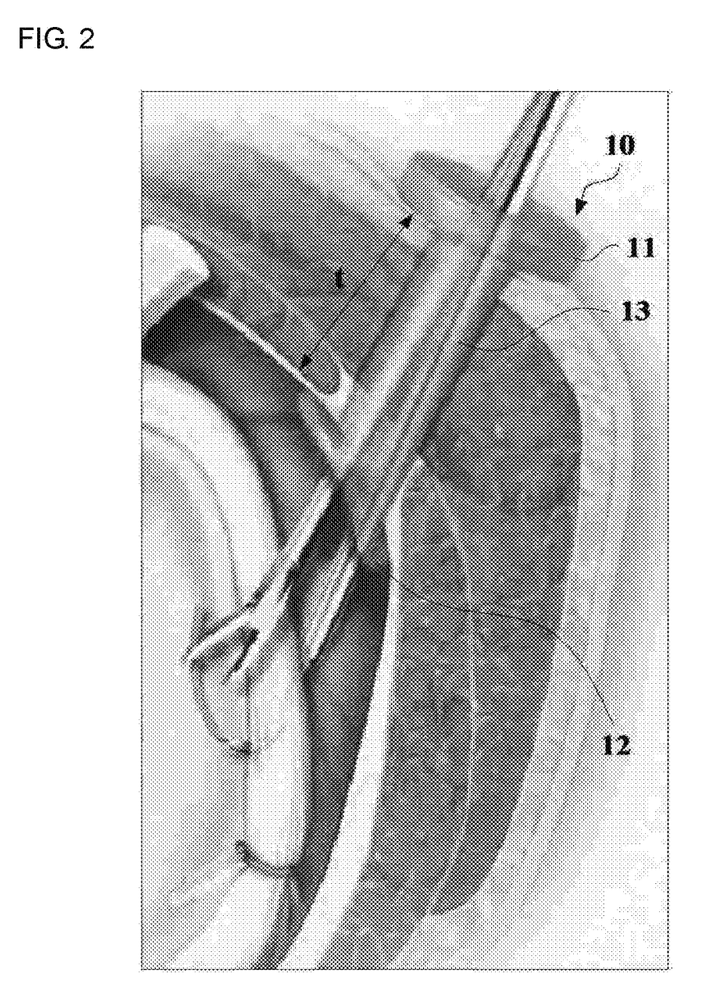
FIG. 2 illustrates a glenohumeral operation using the conventional cannula.
Figure 3:
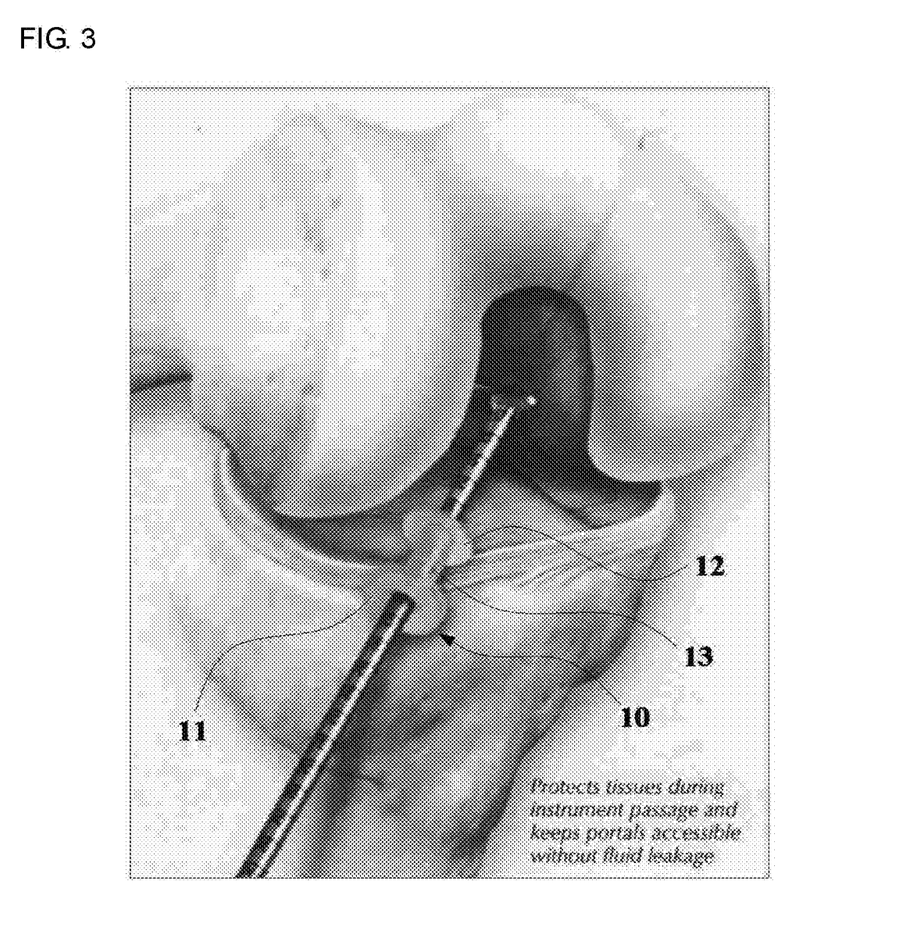
FIG. 3 illustrates a knee bone operation using the conventional cannula.

That is to say, a cannula secures a state where a skin of a human body is incised during a medical treatment, e.g., a rotator cuff operation as shown in FIG. 1, a bankart repair, a long head of biceps tendon or a glenohumeral operation as shown in FIG. 2, and a knee bone, a semilunar cartilage or a cross ligament operation using a joint endoscope as shown in FIG. 3.

Figure 4:
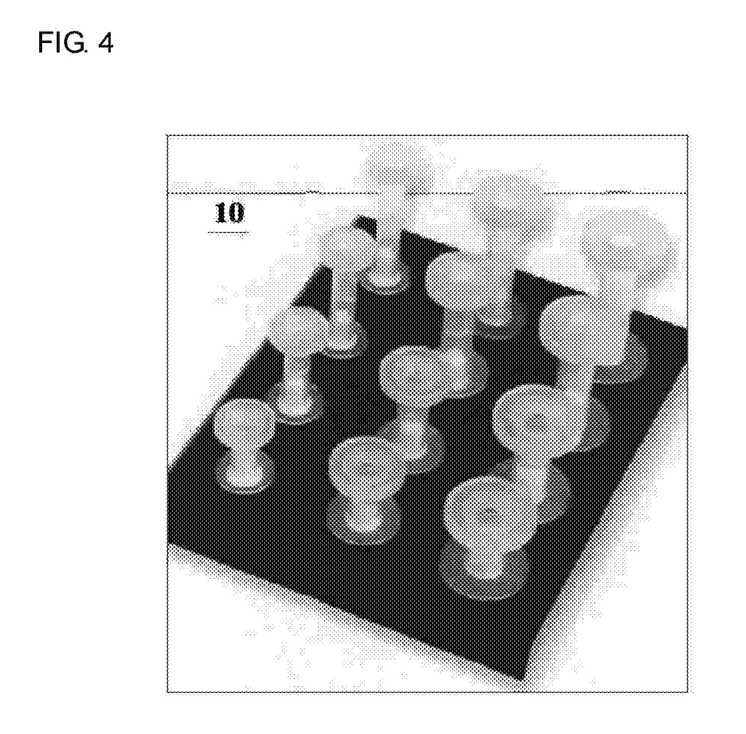
FIG. 4 illustrates conventional cannulas having various lengths.

For the purpose as described above, a conventional cannula 10 includes a pipe-like main body 13 having a through hole formed therein, an outer support plate 11 provided at an end of the main body 13, and an inner support plate 12 provided at another end of the main body 13.

When the cannula 10 is inserted into a human body after a skin is incised, the outer support plate 11 is brought into contact with an outside skin and the inner support plate 12 is brought into contact with and fixedly-supported by an inside skin, so that an incision portion between the outside and the inside skin is secured by the main body 13.

In the conventional cannula 10, the outer support plate 11 and the inner support plate 12 are fixed at respective ends of the main body 13, which raises a problem in that one among a plurality of cannulas having different lengths from each other is required to be prepared and selected depending on a distance t from the outside skin to a medical treatment region of the human body.

Further, the conventional cannula 10 has a drawback in that the operation time is lengthened because the distance t from the outside skin to the medical treatment region is required to be measured in order to select a cannula suitable for the distance t. Furthermore, a selected cannula is required to be replaced with other one, if an error occurs during the distance measurement. A replacement of the cannula results in an enlargement of an incision portion of the human body, which also enlarges a scar on the human body and lengthens the recovery time after the medical treatment.

SUMMARY OF THE INVENTION

In view of the above, the present invention provides a length adjustable cannula allowing a stable installation irrespective of a distance from an outside skin to a medical treatment region of the human body, by adjusting a position of an outer support plate based on the distance such that the outer support plate is brought into contact with and supported by the outside skin and an inner support plate inserted into the human body is brought into contact with and supported by an inside skin.

Further, the present invention provides a length adjustable cannula capable of being used regardless of patients having different distances from outside skins to inside skins without measuring the distance from the outside skin to the inside skin for selecting a cannula having a suitable length for a patient, and thus shortening the operation time, facilitating the medical treatment, and eliminating the necessity for replacement of the cannula due to mismeasurement of the distance to thereby prevent enlargement of the incision portion.

In accordance with one aspect of the invention, there is provided a length adjustable cannula to be inserted into a human body when a medical treatment is performed thereon to thereby connect an inside and an outside of the human body, the cannula including: a pipe-like main body having a through hole formed therein and an outer circumferential surface on which a screw thread is formed, the through hole allowing medical instruments to pass therethrough; a base grip provided at an end of the main body, the grip being disposed at the outside of the human body when the cannula is inserted into the human body; an inner support plate provided at another end of the main body, the inner support plate being disposed at the inside of the human body when the cannula is inserted into the human body; and an outer support plate thread-coupled with the outer circumferential surface of the main body, the outer support plate being movable along the screw thread in a lengthwise direction of the main body, wherein a position of the outer support plate is adjusted based on a distance from an outside skin to a medical treatment region of the human body, such that the outer support plate is brought into contact with the outside skin and the inner support plate is brought into contact with and supported by an inside skin of the human body, and wherein the inner support plate has a shade-like shape descending toward the outer support plate and two or more grooves are formed on surfaces of the inner support plate.

Preferably, a support plate grip is provided at the outer support plate.

Preferably, the base grip, the inner support plate and the outer support plate are made of silicon having elasticity, and the body is made of a plastic material.

Preferably, a reinforcing plate is fixed on a surface of the outer support plate facing the outside of the human body when the cannula is inserted into the human body.

Preferably, a flange configured to extend in one direction, to cover soft tissues formed in a patient's body, and thus to allow an administrator of medicine to facilely secure a clear view is formed at the inner support plate.

According to the present invention, the position of the outer support plate can be adjusted based on the distance, such that the outer support plate is brought into contact with and supported by the outside skin and the inner support plate inserted into the human body is brought into contact with and supported by the inside skin. Accordingly, the cannula can be stably installed irrespective of the distance from the outside skin to the medical treatment region of the human body.

Further, because medical treatments for patients having different distances from outside skins to inside skins can be carried out by using the single cannula 20, measurement of the distance from the outside skin to the inside skin for selecting a cannula having a suitable length for a patient need not be carried out, which shortens the operation time, facilitates the medical treatment, and eliminates the necessity for replacement of the cannula due to mismeasurement of the distance to thereby prevent enlargement of the incision portion.

Further, according to the present invention, since the soft tissues in the patient's body is covered by the flange formed at the inner support plate, it is possible to secure the view of camera for allowing the visual identification of the administrator of medicine, thereby improving the speed and accuracy of the medical treatment.

BRIEF DESCRIPTION OF THE DRAWINGS

The above features of the present invention will become apparent from the following description of embodiments, given in conjunction with the accompanying drawings, in which.

DETAILED DESCRIPTION OF THE EMBODIMENTS

Hereinafter, embodiments of the present invention will be described in detail with reference to the accompanying drawings, which form a part hereof. Like reference numerals will be given to like parts having substantially the same functions, and redundant description thereof will be omitted in the specification and the accompanying drawings.

Figure 5:
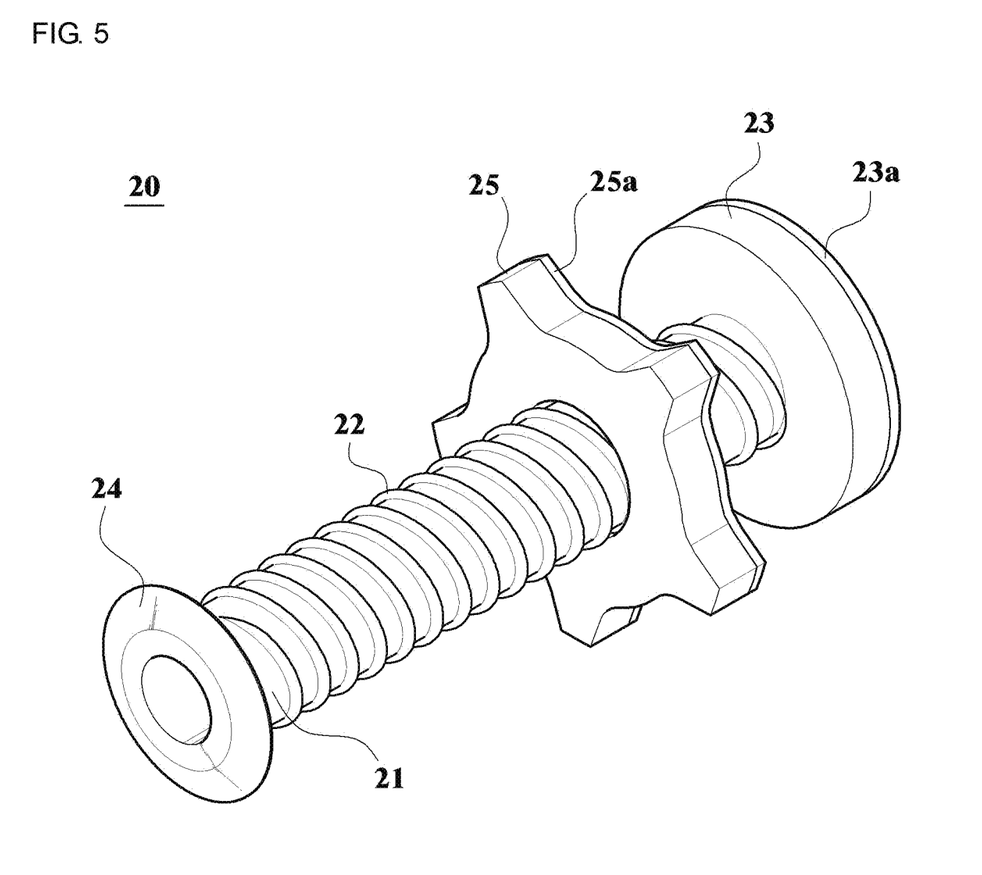
FIG. 5 illustrates a perspective view of a length adjustable cannula in accordance with an embodiment of the present invention.

As shown in FIG. 5, a length adjustable cannula 20 includes a pipe-like main body 21 having a through hole (not shown) formed therein and an outer circumferential surface on which a screw thread 22 is formed, the through hole allowing medical instruments to pass therethrough in a lengthwise direction thereof; a base grip 23 provided at an end of the main body 21; an inner support plate 24 provided at another end of the main body 21; and an outer support plate 25 thread-coupled with the outer circumferential surface of the main body 21, the outer support plate being movable along the screw thread in a lengthwise direction of the main body 21.

When a skin of the human body is incised and the cannula 20 is fixedly-inserted into the human body, an incision portion is secured by the cannula 20 and the medical instruments are inserted into the through hole formed in the main body 21 of the cannula 20 to thereby carry out a medical treatment. That is to say, the cannula 20 is inserted into the human body and used as a passage connecting the inside and the outside of the human body during the medical treatment.

Unlike the conventional cannula, the outer support plate 25 is thread-coupled with the screw thread 22 formed on the outer circumferential surface of the main body 21 and moves along the screw thread 22 in the lengthwise direction of the main body 21. Accordingly, a position of the outer support plate 25 can be adjusted based on a distance from an outside skin to a medical treatment region, e.g., an inside skin, of the human body, such that the outer support plate 25 is brought into contact with the outside skin and the inner support plate 24 is brought into contact with and supported by the inside skin of the human body.

Because the cannula 20 is fixed in such a manner that the outer support plate 25 and the inner support plate 24 press the outside and the inside skin, respectively, medical treatments for patients having different distances from outside skins to inside skins can be carried out by using a single cannula 20.

Further, because the cannula 20 can be used regardless of patients, measurement of the distance from the outside skin to the inside skin for selecting a cannula having a suitable length for a patient need not be carried out, which shortens the operation time, facilitates the medical treatment, and eliminates the necessity for replacement of the cannula due to mismeasurement of the distance to thereby prevent enlargement of the incision portion.

To be specific, since the main body 21 has a pipe-like shape and the through hole is formed in the main body 21 along the lengthwise direction of the main body 21, the medical instruments inserted via an end of the through hole disposed outside of the human body when the cannula 20 is inserted into the human body can reach the medical treatment region via another end of the through hole disposed inside of the human body when the cannula 20 is inserted into the human body.

The medical instruments may be a medical pincette, medical scissors and a medical knife for use in various medical treatments, e.g., a rotator cuff operation, a glenohumeral operation and knee bone operation. The medical instruments also may be a cannula for injecting medicines into a human body or ejecting body fluids from the human body, an injector for injecting plug materials for osteoporosis treatments and the like.

Further, the screw thread 22 is formed on the outer circumferential surface of the main body 21, and the outer support plate 25 is thread-coupled with the screw thread 22 via a thread hole (see, reference symbol H in FIG. 7) formed at a center portion of the outer support plate 25.

The inner support plate 24 is fixedly-provided at an end of the main body 21. Accordingly, an administrator of medicine can insert the cannular 20 into the human body while holding the inner support plate 24 by using an additional instrument and adjust the length of the cannula 20 by rotating the outer support plate 25 to change the position of the outer support plate 25 while holding the base grip 23.

The base grip 23 is also made of silicon being light. Preferably, a reinforcing layer 23a made of a solid material, e.g., a plastic, may be fixedly-stacked on a top surface of the base grip 23 facing the outside of the human body when the cannula 20 is inserted into the human body, thereby preventing a deformation of the base grip 23.

The inner support plate 24 is fixed at an end of the main body 21 disposed inside of the human body when the cannula 20 is inserted into the human body, i.e., at an end opposite to the end where the base grip 23 is provided. Basically, the inner support plate 24 has a disk-like shape. The inner support plate 24 is brought into contact with and supported by the inside skin when the cannula 20 is inserted into the human body via the incision portion, and thus the inner support plate 24 and the outer support plate 25 respectively press the inside skin and the outside skin in opposite directions to each other, thereby fixing the cannula 20 inserted into the human body.

The inner support plate 24 may have a shade-like shape descending toward the outer support plate 25. During an insertion of the cannula 20 into the human body, this shade-like shape makes the inner support plate 24 bend in an opposite direction to the insertion direction, thereby facilitating the insertion. After the insertion, since the inner support plate 24 is brought into contact with and firmly supported by the inside skim, this shade-like shape makes the inner support plate 24 act like an anchor and the cannula 20 is prevented from moving or swaying.

Figure 6:
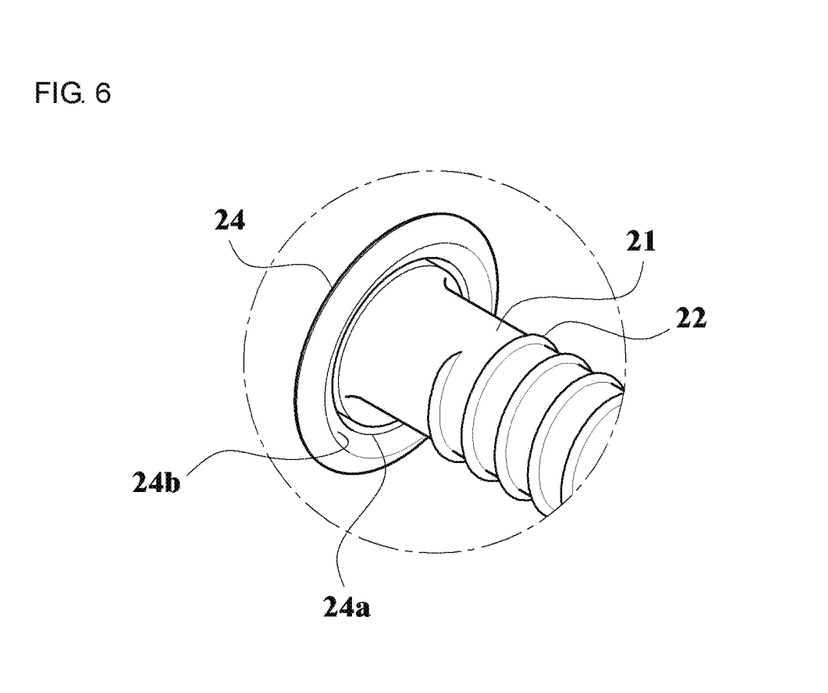
FIG. 6 illustrates an enlarged perspective view of an inner support plate of the length adjustable cannula.

The inner support plate 24 may have bending grooves 24a and 24b formed on a surface facing the outer support plate 25, as shown in FIG. 6. However, bending grooves may be formed on the opposite surface of the inner support plate 24, or, a bending groove may be formed on each of the surfaces of the inner support plate 24.

In FIG. 6, the bending groove 24a is a circular groove formed on the plane surface of the shade-like inner support plate 24 and the bending groove 24b is a circular groove formed on the slanting surface of the shade-like inner support plate 24. However, two or more bending grooves may be formed in a concentric manner.

The bending grooves 24a and 24b facilitate bending of the inner support plate 24 in both one direction and an opposite direction thereto. Accordingly, both the insertion and drawing out of shade-like cannular 20 to and from the human body can be also facilitated.

Figure 9:
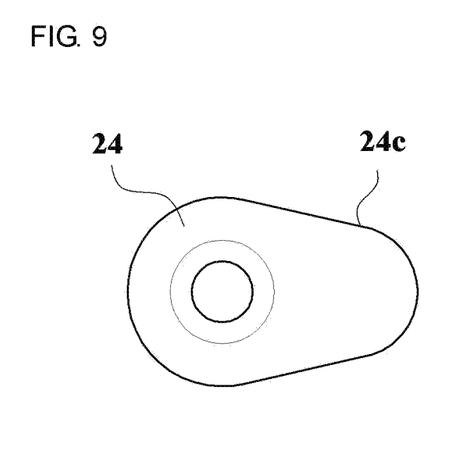
FIG. 9 illustrates another embodiment of an inner support plate of the length adjustable cannula in accordance with the present invention.
Figure 10:
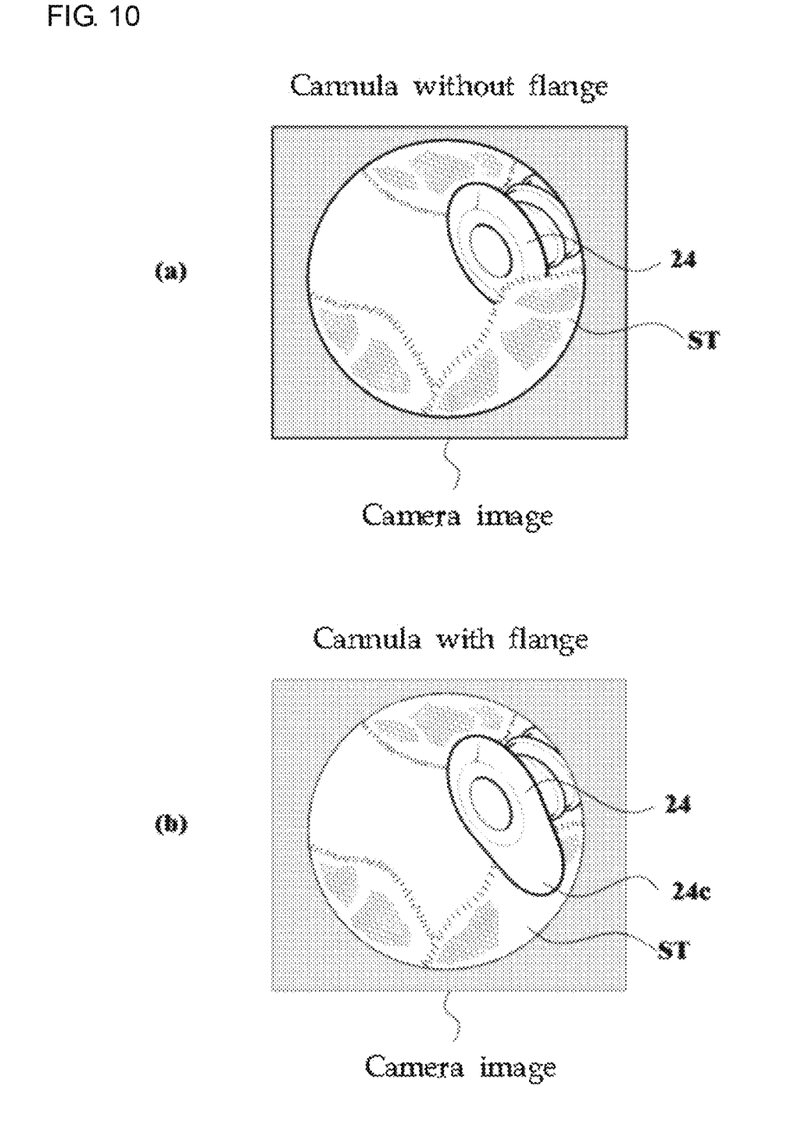
FIG. 10 illustrates an operational relationship of a flange formed at the inner support plate of the length adjustable cannula in accordance with the present invention.

Further, as illustrated in FIG. 9, a flange 24c extending in one direction is formed at the inner support plate 24 to allow the administrator of medicine to facilely secure a clear view. That is, the administrator of medicine moves the camera, which is inserted into a body or an incision portion of a patient, near the cannula 20 to facilely select a position of the cannula 20 inserted through another incision portion of the patient, and performs a medical treatment while monitoring an image sent from the camera. At this time, many fiber-shaped soft tissues are in the body of the patient. The soft tissues obstruct a field of vision of the administrator, and thus it is difficult to smoothly perform the medical treatment (referring to FIG. 10a).

Therefore, the flange 23c formed at the inner support plate 24 is directed in a direction, to which the camera is inserted, to cover part of the soft tissues obstructing a view of the camera, such that the administrator may secure the field of vision, and the medical treatment may be smoothly performed (FIG. 10b).

The outer support plate 25 is brought into contact and supported by the outside skin of the human body, and fixes the cannula 20 by pressing the skin of the human body together with the inner support plate 24. The outer support plate 25 is configured to be movable along the main body 21 in a lengthwise direction of the main body 21, such that a length of the cannula 20 corresponding to a distance between the inner support plate 24 and the outer support plate 25 can be adjusted.

Figure 7:
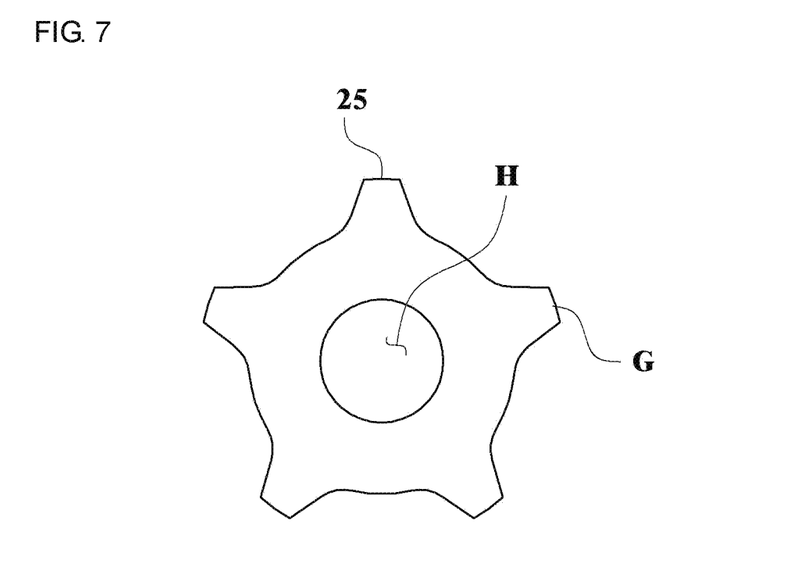
FIG. 7 illustrates a front view of an outer support plate of the length adjustable cannula.

For the purpose as described above, the outer support plate 25 has a thread hole H formed at a central portion thereof, as shown in FIG. 7. When the main body 21 is inserted via the thread hole H and the screw thread 22 and the thread hole H are thread-coupled, the outer support plate 25 can move along the main body 21 in the lengthwise direction of the main body 21, i.e., in the forward and backward direction of the screw.

Further, a support plate grip G is protrusively formed at the outer circumferential surface of the outer support plate 25. Accordingly, an administrator of medicine can easily adjust the position of the outer support plate 25 by rotating the outer support plate 25 while grasping the support plate grip G.

Basically, the outer support plate 25 is made of silicon, and a reinforcing plate 25a made of a solid material, e.g. a plastic, may be fixedly-stacked on a surface of the outer support plate 25 facing the outside of the human body when the cannula 20 is inserted into the human body. That is to say, the surface where the reinforcing plate 25a is provided is a surface opposite to the surface brought into contact with the outside skin when the cannula 20 is inserted into the human body. The reinforcing plate 25a prevents the outer support plate 25 from being excessively deformed.

That is to say, the outer support plate 25 may have a two-layered structure, in which a first layer brought into contact with the outside skin when the cannula 20 is inserted into the human body is made of soft silicon and a second layer, i.e., the reinforcing plate 25a, stacked on the first layer is made of a solid material, thereby preventing the outer support plate 25 from being deformed.

In addition, the body 21 forming the cannula 20, the base grip 23, the inner support plate 12 and the outer support plate 25 are made of silicon being harmless to humans, being light and soft, and having elasticity. At this time, the body 21 inserted into the patient's body is vertically inserted into the patient's body, and made of a soft plastic material, unlike the base grip 23, the inner support plate 12 and the outer support plate 25, such that medical instruments (not shown) may be easily inserted through a through hole H.

Figure 8:
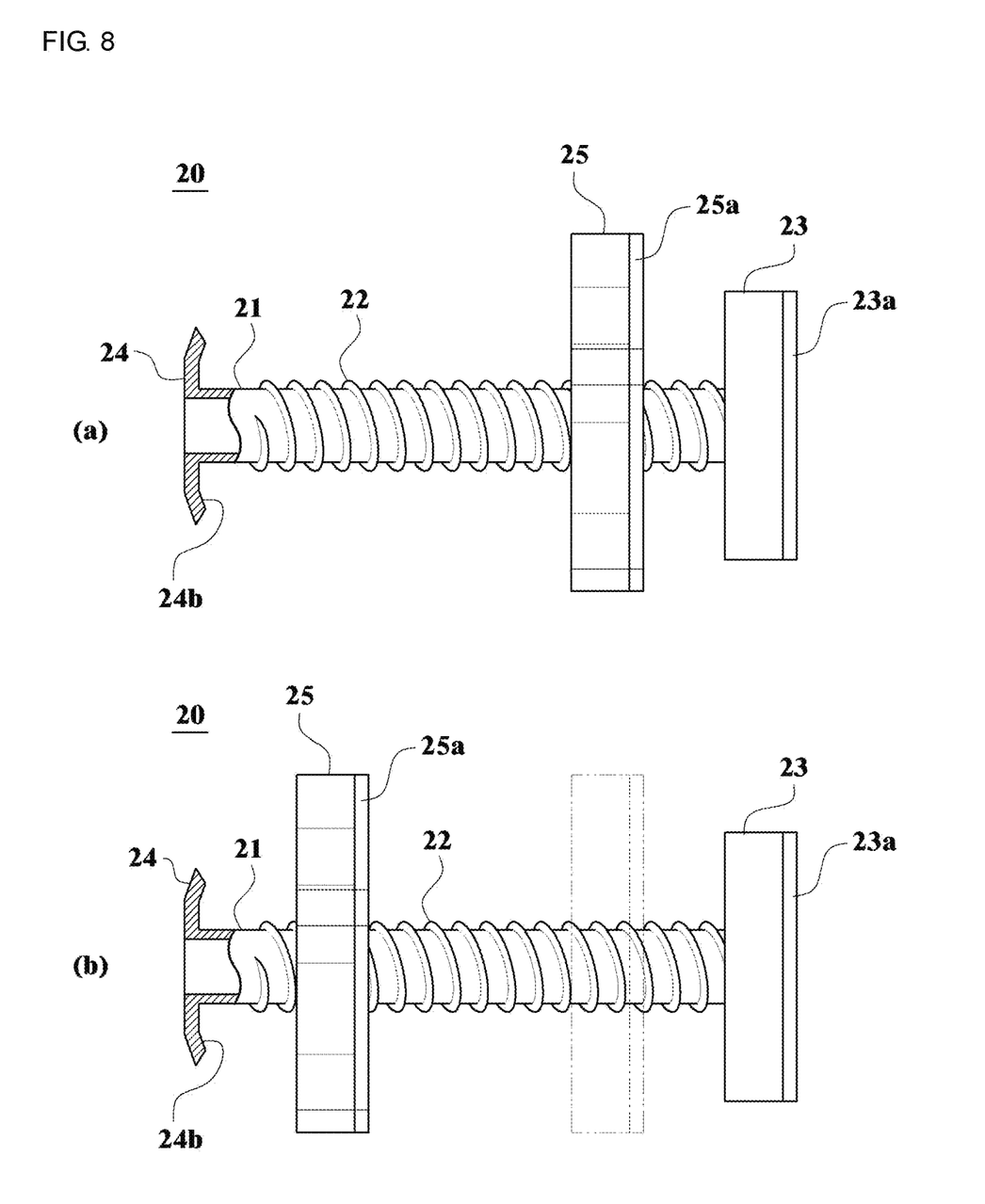
FIG. 8 illustrates an operational status view of the length adjustable cannula.

As shown in FIG. 8, the position of the outer support plate 25 can be adjusted based on the distance from the outside skin to the medical treatment region of the human body by moving the outer support plate 25 along the main body 21. Accordingly, the cannula 20 can be stably installed regardless of the distance from outside skin to the medical treatment region of the human body, and thus a plurality of cannulas having different lengths from each other need not be prepared to perform a medical treatment on a patient.

Further, because medical treatments for patients having different distances from outside skins to inside skins can be carried out by using the single cannula 20, measurement of the distance from the outside skin to the inside skin for selecting a cannula having a suitable length for a patient need not be carried out, which shortens the operation time, facilitates the medical treatment, and eliminates the necessity for replacement of the cannula due to mismeasurement of the distance to thereby prevent enlargement of the incision portion.

In the above-described embodiments, the outer support plate 25 is brought into contact with and supported by the outside skin of the human body and the inner support plate 24 is brought into contact with and supported by the inside skin of the human body. However, it is obvious to those skilled in the art that the inside skin may be various medical treatment regions by which the inner support plate 24 is supported when the cannula is inserted into the human body.

While the invention has been shown and described with respect to the embodiments, it will be understood by those skilled in the art that various changes and modification may be made without departing from the scope of the invention as defined in the following claims.

What is claimed is:

1. A length adjustable cannula to be inserted into a human body when a medical treatment is performed thereon to thereby connect an inside and an outside of the human body, the cannula comprising:
    a pipe-like main body extending in a direction of a longitudinal axis positioned therethrough, the pipe-like main body having a through hole formed therein and an outer circumferential surface on which a screw thread is formed, the through hole allowing medical instruments to pass therethrough;
    a base grip provided at a first end of the pipe-like main body, the base grip comprising a top surface having a first perimeter made of a first material and a reinforcing layer having a second perimeter made of a second material different from the first material and fixedly-stacked on the top surface of the base grip wherein the second perimeter of the reinforcing layer is fully positioned above the first perimeter of the base grip, wherein the first perimeter and the second perimeter form an outside surface of the first end of the pipe-like main body and the base grip is disposed at an outside of a human body when the cannula is inserted into the human body;
    an inner support plate provided at another end of the pipe-like main body, the inner support plate being disposed at an inside of the human body when the cannula is inserted into the human body; and
    an outer support plate threadedly coupled with the outer circumferential surface of the pipe-like main body, the outer support plate being movable along the screw thread in a lengthwise direction of the pipe-like main body,
    wherein a position of the outer support plate is adjusted based on a distance from an outside skin to a medical treatment region of the human body, such that the outer support plate is brought into contact with the outside skin and the inner support plate is brought into contact with and supported by an inside skin of the human body,
    wherein a reinforcing plate is fixed on a surface of the outer support plate facing the outside of the human body when the cannula is inserted into the human body, wherein the reinforcing plate is made of a different material than the outer support plate, and
    wherein the inner support plate has a shade-like shape descending toward the outer support plate and two or more grooves are formed on surfaces of the inner support plate.

2. The cannula of claim 1, wherein a support plate grip is provided at the outer support plate.

3. The cannula of claim 1, wherein the base grip, the inner support plate and the outer support plate are made of silicon having elasticity, and the pipe-like main body is made of a plastic material.

4. The cannula of claim 1, wherein a flange configured to extend in one direction, to cover soft tissues formed in a patient's body, and thus to allow an administrator of medicine to facilely secure a clear view is formed at the inner support plate.

* * * * *